(12) United States Patent
Morales et al.

(10) Patent No.: US 10,023,899 B2
(45) Date of Patent: Jul. 17, 2018

(54) COMPOSITION FROM LOBSTER HEMOCYTE EXTRACTS FOR DETECTION OF LIPOPOLYSACCHARIDES, PEPTIDOGLYCANS AND 1,3-BETA-D-GLUCANS

(71) Applicants: Centro de Investigacion Y Desarrollo de Medicamentos (CIDEM), La Habana (CU); Universidad de La Habana, La Habana (CU)

(72) Inventors: Rolando Perdomo Morales, La Habana (CU); Vivian Montero Alejo, La Habana (CU); Erick Perera Bravet, La Habana (CU); Jorge Ernesto Calero Carbonell, La Habana (CU); Zenia Pardo Ruiz, La Habana (CU); Marlene Porto Verdecia, La Habana (CU); Yamile Vega Hurtado, La Habana (CU)

(73) Assignees: Centro de Investifacion Y Desarrollo de Medicament (CIDEM), Havana (CU); Universidad de La Habana, Havana (CU)

( * ) Notice: Subject to any disclaimer, the term of this patent is extended or adjusted under 35 U.S.C. 154(b) by 159 days.

(21) Appl. No.: 14/368,697

(22) PCT Filed: Dec. 27, 2012

(86) PCT No.: PCT/CU2012/000009
§ 371 (c)(1),
(2) Date: Jun. 25, 2014

(87) PCT Pub. No.: WO2013/113296
PCT Pub. Date: Aug. 8, 2013

(65) Prior Publication Data
US 2014/0356889 A1    Dec. 4, 2014

(30) Foreign Application Priority Data
Dec. 27, 2011    (CU) .......................... CU/P/2011/0243

(51) Int. Cl.
*C12Q 1/26* (2006.01)
*C12Q 1/04* (2006.01)
*C12Q 1/37* (2006.01)

(52) U.S. Cl.
CPC ............... *C12Q 1/26* (2013.01); *C12Q 1/04* (2013.01); *C12Q 1/37* (2013.01)

(58) Field of Classification Search
CPC ............... C12Q 1/04; C12Q 1/37; C12Q 1/26
See application file for complete search history.

(56) References Cited

U.S. PATENT DOCUMENTS

| | | |
|---|---|---|
| 3,954,663 A | 5/1976 | Yamamoto et al. |
| 4,023,802 A | 5/1977 | Jepson et al. |
| 4,107,077 A | 8/1978 | Sullivan, Jr. et al. |
| 4,188,264 A | 2/1980 | Iwanaga et al. |
| 4,279,774 A | 7/1981 | Lindsay et al. |
| 4,322,217 A | 3/1982 | Dikeman |
| 4,510,241 A | 4/1985 | Mills |
| 4,970,152 A | 11/1990 | Ashida et al. |
| 5,047,353 A | 9/1991 | Tsuchiya et al. |
| 5,155,032 A | 10/1992 | Tanaka et al. |
| 5,179,006 A | 1/1993 | Matuura et al. |
| 5,310,657 A | 5/1994 | Berzofsky |
| 5,401,647 A | 3/1995 | Tanaka et al. |
| 5,605,806 A | 2/1997 | Tanaka et al. |
| 5,702,882 A | 12/1997 | Tamura et al. |
| 5,998,389 A | 12/1999 | Loverock |
| 7,598,054 B2 | 10/2009 | Kovalenko et al. |
| 2002/0197662 A1 | 12/2002 | Auh et al. |
| 2003/0104501 A1 | 6/2003 | Jordan et al. |

FOREIGN PATENT DOCUMENTS

WO    WO 2007127459 A2 * 11/2007 ............... C12Q 1/04

OTHER PUBLICATIONS

Lin Y-C. et al., "Identification and phylogenetic analysis on lipopolysaccharide and b-1,3-glucan binding protein (LGBP) of kuruma shrimp *Marsupenaeus japonicus*", Developmental and Comparative Immunology, 2008, vol. 32, pp. 1260-1269.*
Jayraj S.S. et al. "Isolation, purification and characterization of b-1,3-glucan binding protein from the plasma of marine mussel *Perna viridis*", Fish & Shellfish Immunology, 2008, vol. 24, pp. 715-725.*
Perdomo-Morales et al., "The Trypsin Inhibitor Panulirin Regulates the Prophenoloxidase-activating System in the Spiny Lobster *Panulirus argus*", The Journal of Biological Chemistry, Nov. 2013, vol. 288, No. 44, pp. 31867-31879.*
Innate Immunity; Ruslan Medzhitov, Ph.D. and Charles Janeway, Jr., M.D.; (Review Articles) New England Journal of Medicine; Aug. 3, 2000; pp. 338-344.
Phenoloxidase Activity in the Hemolymph of the Spiny Lobster *Panulirus argus*; R. Perdome-Morales et al.; Fish & Shellfish Immunology 23 (2007); pp. 1187-1195.
In the Spiny Lobster (*Panulirus interruptus*) the Prophenoloxidase is Located in Plasma not in Haemocytes; Jorge Hernandez Lopez et al.; Fish & Shellfish Immunology 14 (2003); pp. 105-114.

* cited by examiner

*Primary Examiner* — Satyendra K Singh
(74) *Attorney, Agent, or Firm* — Lackenbach Siegel, LLP

(57) ABSTRACT

The present invention relates to the pharmaceutics, biotechnological and chemical, and particularly to a process for preparing a composition for detecting and measuring the concentration of endotoxins or lipopolysaccharides, peptidoglycans and (1,3)-β-D-glucans, using an extract from the hemocytes of the lobster as a starting material, the changes to the composition to increase the sensitivity, and processes for measuring endotoxins, peptidoglycans and (1,3)-β-D-glucans using said composition.

10 Claims, 3 Drawing Sheets

COMPOSITION FROM LOBSTER HEMOCYTE EXTRACTS FOR DETECTION OF LIPOPOLYSACCHARIDES, PEPTIDOGLYCANS AND 1,3-BETA-D-GLUCANS

PRIOR RELATED APPLICATIONS

This application is a 371 U.S. National Phase Patent Application which claims priority to PCT Patent Application No. PCT/CU2012/000009, filed Dec. 27, 2012 and Cuba Patent Application CU/P/2011/0243, filed Dec. 27, 2011 and incorporates the above-referenced applications in their entireties by reference thereto.

DESCRIPTION OF THE INVENTION

The present invention relates to the field of chemical, pharmaceutical and biotechnology, particularly with the detection of microorganisms and structures associated to their cell wall such as lipopolysaccharides (LPS) or endotoxins from Gram negative bacteria, peptidoglycans (PG) from Gram negative and positive, and (1,3)-β-D-glucans (BG) from fungi and yeasts. The present invention also has application in the assessment of microbial contamination in ultrapure water as that used in the semiconductor industry, and as a diagnostic tool for the clinical laboratory.

The innate immune system provides very effective response mechanisms for the detection of microorganisms through recognition of molecular structures preserved and shared by a great number of microbes. These structures known as pathogen-associated molecular patterns (PAMPs) are not found in the host and are essential for the survival or pathogenicity of microorganisms. Among the best-characterized PAMPs are LPS, BG and PG, among others [Medzhitov and Janeway, The New England Journal of Medicine, 343(5):338-344, 2000].

It has been long established that endotoxins are the most relevant TAMP or exogenous pyrogen for the pharmaceutical and biotechnological industries because of their remarkable biological potency, ubiquity, resistance to conventional sterilization methods, and high probability of contaminating parenteral solutions [Williams K. L. Endotoxin Relevance and Control Overview; in Williams, K. L. (eds). Endotoxins, Pyrogens, LAL Testing and Depyrogenation. Third edition. Healthcare Report, New York, London. 2007, 27-46]. Furthermore, they are the main responsible of endotoxic shock associated with sepsis caused by Gram negative bacteria, and constitute the first alarm signal indicating the presence of these bacteria to the innate immune system. Access of LPS into the bloodstream produces profound deleterious effects on human health, such as systemic inflammatory response syndrome (SIRS), multiple organ failure (MOF), shock, and death [Opal S M, Contrib Nephrol 167, 14-24, 2010, Hodgson J C, J Comp Pathol 135, 157-175, 2006].

BACKGROUND OF THE PRIOR ART

The *Limulus* Amebocyte Lysate test (LAL) has been widely used for the detection of bacterial endotoxins, especially in the quality control of parenteral pharmaceutical and biotechnological products (U.S. Pat. No. 4,107,077, U.S. Pat. No. 4,279,774, U.S. Pat. No. 4,322,217, U.S. Pat. No. 3,954,663, U.S. Pat. No. 4,038,029, U.S. Pat. No. 4,188,264, U.S. Pat. No. 4,510,241, U.S. Pat. No. 5,310,657).

The LAL reagent is prepared from an extract of amebocytes present in the hemolymph of horseshoe crabs. It consists of a cascade of trypsin-like serine peptidases, which is activated in presence of endotoxins and (1,3)-β-D-glucans through the Factors C and G, respectively. The reagent is based on the clotting response of horseshoe crabs, which is part of its innate immune system. A similar system has not been found in other invertebrate species so far [Iwanaga S y Lee B L, J Biochem Mol Biol 38, 128-150, 2005].

Endotoxin-specific LAL reagents have been obtained by separating Factor G sensitive to (1,3)-β-D-glucans, leaving remaining components of the enzymatic cascade of the LAL (U.S. Pat. No. 5,401,647, U.S. Pat. No. 5,605,806, US20030104501) or inhibiting its activation (U.S. Pat. No. 5,047,353, U.S. Pat. No. 5,155,032, U.S. Pat. No. 547,984, U.S. Pat. No. 5,702,882, U.S. Pat. No. 5,998,389, U.S. Pat. No. 5,179,006).

Horseshoe crabs are marine arthropods known as living fossils because they have evolved little in the last 300 million years. There are four species of horseshoe crabs from which a similar reagent can be obtained.

The species *Tachypleus tridentatus*, *Tachypleus gigas* and *Carcinoscorpius rotundicauda* are exclusively in Asia. The small population of the last two has never sustained production of the reagent. Moreover, *Tachypleus tridentatus*, commonly known as Chinese horseshoe crab or tri-spine horseshoe crab, had a high population density along the coast of China, especially in the northern South China Sea and in region to the range of Hainan Island. However, recent studies on *T. tridentatus* in Taiwan, Japan, Hong Kong, Thailand and China, have indicated that populations have declined drastically almost to extinction. The main causes are overfishing and pollution of the seas.

Due to the low population density of the Asian species, the LAL reagent marketed is mostly obtained from *Limulus polyphemus*, also known as the American horseshoe crab. The *Limulus* inhabits the US Atlantic coast, from northern Maine to the Yucatan Peninsula and the Gulf of Mexico. The greatest population is found in Delaware Bay but there has been a drastic decline in its numbers and spawning activity [Widener J W and Barlow R B, Biological Bulletin (197): 300-302, 1999]. The main causes have been the habitat loss and use as bait in fishing for oysters and eels [Rudloe A, Journal of Invertebrate Pathology (42):167-176, 1983; Bolton M L, Biologist (49): 193-198, 2002]. Mortality due to bleeding process for the preparation of LAL reagent ranged around 15% [Walls E A and Berkson J, Virginia Journal of Science 51(3):195-198, 2000], but has doubled in the past time, increasing the decline of its population.

According to FAO, due to the high price of the LAL reagent, the narrow range of distribution of horseshoe crabs, and the extremely long time it takes for them to reach sexual maturity, it is easy to reduce the horseshoe crab population below the recovery rate. The four species are in danger of extinction and are included on the Red List of the International Union for the Conservation of Nature and Natural Resources (IUCN).

Considering the current critical situation of the horseshoe crab population, the United States Atlantic States Maritime Fishing Commission (ASMFC) has regulated several aspects concerning fishing and exploitation of the *Limulus*. Regarding the LAL industry, established that specimens cannot be bled to death and must be returned to the capture site marked and in healthy condition within less than 72 hours. It also set annual quotas of animals to be used to produce LAL, and that mortality associated with their handling could not exceed 15% of this quota.

Globally it has raised the need to study alternatives for the detection of endotoxins and other pyrogens before the source of raw material, the hemolymph from *Limulus*, is no longer available. The establishments of annual quota of horseshoe crabs that can be used by the industry to produce LAL, while its demand continues on the rise, coupled with the recession of the population, indicate that it is not possible to sustain the increase in capture and bleeding of horseshoe crabs to produce LAL reagent.

U.S. Pat. No. 4,229,541, U.S. Pat. No. 5,082,782, U.S. Pat. No. 6,790,659 and US20030186432 describes the development of strategies for the in vitro culture of amebocytes as an alternative to the hemolymph of horseshoe crab as natural source of amebocytes for preparing LAL. To date there is no commercial reagent obtained in this way or a project for its obtaining. On the other hand, through a novel methodology it has been successfully cloned and produced the recombinant of the endotoxin-sensitive Factor C from the Singapore horseshoe crab, *Carcinoscorpius rotundicauda*. (U.S. Pat. No. 5,712,144, U.S. Pat. No. 5,858,706, U.S. Pat. No. 5,985,590), and has been established its use for the detection and quantitation of LPS or endotoxin in a similar approach to the natural LAL reagent (U.S. Pat. No. 6,645,724). It have been patented reagent formulations that combine the recombinant Factor C and detergents (US20030054432) or recombinant Factor C or that obtained by purification from natural source in formulations that exhibit increased sensitivity and stability (US20040235080). However, due to the lack of other enzymes naturally present in the reagent, these formulations lack the sensitivity provided by the amplifier effect of the enzymatic cascade, which has been partially solved by employing more sensitive fluorescent substrates. Other components of the LAL cascade such as the clotting enzyme (US20090208995) and the Factor G (US2010011266) have also been produced recombinant.

The LAL reagent and the recombinant Factor C are able to detect LPS, but do not detect PG. However, recent studies show the urgent need to also detect and control the content of PG in formulations for parenteral use, and other solutions and devices that should be non-pyrogenic. The PG are well-conserved components of cell wall of Gram positive and negative bacteria, and are the main responsible for the inflammatory response and its deleterious health consequences caused by Gram positive organisms, including septic shock [Silhavy T J et al., Cold Spring Harbor perspectives in biology 2, a000414, 2010], As the LPS, the PG are able to induce the release of proinflammatory cytokines [Verhoef J and Mattsson E, Trends in Microbiology 3:136-140, 1995; Teti G, Trends in Microbiology 7; 100-101, 1999], are pyrogenic, released into the environment during growth and death of bacteria, and are resistant to ordinary means of sterilization [Moesby L, European Journal of Pharmaceutical Science 35, 442-446, 2008]. Due to the similarities between LPS and PGs it has been proposed that both be granted the same importance [Myhre A E et al., Shock 25 (3):227-35, 2006]. Moreover, the presence of PG can markedly sensitize the inflammatory response induced by LPS by synergism [Takada H et al., Journal of Endotoxin Research 8, 337-342, 2002; Hadley J S et al., Infection and Immunity, 73; 7613-7619, 2005; Wray G M, Shock, 15(2): 135-42, 2001; Shikama Y et al., Innate Immunity, 17(1):345, 2009] or by additive effect [Sprong T, Journal of Leukocyte Biology, 70:283-288, 2001].

Like the LAL cascade for horseshoe crabs, the prophenoloxidase activating system (ProPO system) is an essential component of the humoral innate immune response of invertebrates [Cerenius et al., Trends Immunol. (29):263-271, 2008]. The ability of proPO system to recognize PAMPs through a biosensor(s) and produce a visible and quantifiable response by measuring the enzymatic activity of the prophenoloxidase activating enzyme (ppA) or the phenoloxidase, makes it an attractive candidate for the development of a reagent for the detection of microorganisms and their PAMPs.

The ProPO system comprises a complex array of proteins including pattern-recognition proteins, the ppA and proPO. It has been described in several arthropods that the proPO system is activated in the presence of small amounts of PAMP through a mechanism that has not been fully elucidated. In general, it is known that in presence of PAMP the pro-ppA become active and, through proteolytic attack, converts prophenoloxidase (inactive zymogen) into active phenoloxidase. The phenoloxidase oxidizes monophenols and/or o-diphenols to aminechromes, initiating the synthesis of melanin.

In U.S. Pat. No. 497,052 it is described the development and use of a reagent obtained from the plasma of silkworm larvae (SLP) for the detection of BG and PG by determining phenoloxidase activity or ppA peptidase activity. It also comprises reagent modifications pursuing the specific determination of BG or PG. Based on this invention, U.S. Pat. No. 5,585,248 describes the use of synthetic sensitive chromogenic substrates for detecting ppA activity. In U.S. Pat. No. 6,274,565 B1 is protected a modification of the reagent that allows specific detection of PG by inhibiting the activation pathway mediated by BG. The assay SLP appears to be particularly useful in the detection of bacterial contamination in platelets (U.S. Pat. No. 7,598,054 B2). Also making use of the proPO system, U.S. Pat. No. 6,987,002 B2 and 2002/0197662 A1 describe a reagent obtained from whole hemolymph of insect larva (*Tenebrio molitor* or *Holotrichia diomphalia*) for detection and quantification of (1,3)-β-D-glucans.

The proPO system in the spiny lobster *P. argus* is found in the hemocytes [Perdomo-Morales et al., Fish Shellfish Immunol (23):1187-1195, 2007], and is capable of being activated in the presence of low concentrations of PG, BG and LPS. There are at least two peptidases related with the activation of proPO zymogen, one is calcium-dependent and the other not. The proPO system is regulated by a peptidase inhibitor of 5 kDa and net positive charge. The separation of the inhibitor from the active components of the system substantially increases the sensitivity of the response to PG, BG and LPS. The proPO system of the lobster also includes a LPS and BG recognizing protein (LGBP), which is localized in the plasma fraction of hemolymph. LGBP become activated upon binding to LPS and BG and is capable to increase the phenoloxidase activity in the lysate by increasing ppA activity.

The composition we are presenting here for first time, consist in an aqueous extract of hemocytes from the hemolymph of lobsters, hereafter referred as Lobster Hemocyte Lysate (LHL). The active component of interest in the LHL is the proPO system, and the composition is directed to the detection and quantitation of LPS, PG and BG. The term lobster or lobsters in this document refers to species listed within infraorders Astacidea, Palinura (Achelata) and Thalassinidea, Reptantia (macrura), Order Decapoda, class Crustacea, Phylum Arthropoda.

Although lobsters are also subject to overfishing in some regions, are very abundant species representing the major fishery resource in many countries (eg, Cuba, Brazil, Australia, USA, etc.). Production of the present composition does not affect the availability of these animals for human consumption as food because the hemolymph is a byproduct that is usually discarded. Lobster is one of the largest crustaceans, and presents a significant volume of hemolymph readily available.

For the preparation of LHL, the hemolymph is withdrawn using a suitable anticoagulant that prevent plasma coagulation, but preferably that avoid both plasma clotting as well as the activation and clump of cells. As anticoagulants can be used an isotonic solution containing methyl xanthine derivatives such as theophylline, theobromine or caffeine, or salts thereof, or reagents capable of modifying sulfhydryl groups (—SH) as cysteine, iodoacetamide and N-ethylmaleimide. Also suitable are solutions containing chelating agents, having a pH between 4.5-8 provided by a suitable buffer, for example, the modified Alsever anticoagulant (27 mM sodium citrate, 336 mM NaCl, 115 mM glucose, 9 mM EDTA, pH 7) or citrate-EDTA anticoagulant (0.4 M NaCl, 0.1 M glucose, 30 mM trisodium citrate, 26 mM citric acid and 10 mM EDTA, pH 4.6). Modified Alsever anticoagulant is preferred, using a proportion hemolymph:anticoagulant 1:1 (v/v).

The hemocytes are separated from plasma by centrifugation at 700 g for 10 min at 4° C. The plasma (supernatant) is discarded, and the sedimented hemocytes are washed to remove residual plasma components. For this purpose, the hemocytes are resuspended with anticoagulant to a volume no greater than that corresponding to the initial mixture of hemolymph:anticoagulant, followed by another identical centrifugation cycle. The hemocytes should be washed at least twice. The washed hemocyte pellet is suspended in lysis buffer, preferably with a volume between 1 and 10 ml. The lysis buffer may contain NaCl at a concentration between 0.001 and 600 mM, agents capable of stabilizing enzymes (stabilizers), and a pH between 5 and 8.5 provided by a suitable buffer that does not sequester divalent cations. The lysis buffer 50 mM Tris-HCl, pH 7.5, 450 mM NaCl is preferred.

The hemocytes are lysed using a suitable disruption method among those commonly used in biochemistry for preparation of cell extracts, which can be mechanical, chemical or enzymatic. Considering the characteristics of these cells, the most suitable rupture methods are osmotic shock, freeze/thawing, homogenization by stirring (vortex) or manual (bounce and Potter-Elvehjemem), and ultrasonication. The hemocytes homogenate is centrifuged at 13 000 rpm at 4° C. for 30 min to obtain the clarified supernatant or LHL.

The present invention includes a modification for increasing the sensitivity of the LHL response to LPS, PG and BC. This modification is based on eliminating or inactivating peptidase inhibitors present in the LHL. The inhibitors can be removed by separation techniques based on molecular size and shape, charge or affinity. Preferably it will be employed procedures based on size exclusion as gel filtration chromatography, ultrafiltration and diafiltration. For gel filtration chromatography, resins with an exclusion limit between 10 and 60 kDa should be used, preferably 30 kDa. The chromatographic fractionation is performed at a flow rate between 3 and 60 cm/h, preferably at 9 cm/h, and the sample volume applied should be between 1 and 5% of the total column volume, preferably 3%. Under these conditions, the remaining active proteins of the proPO system elutes at the void volume of the column. When using ultrafiltration and diafiltration, membranes with cutoff between 5 and 60 kDa are used, preferably between 10 and 40 kDa. The LHL without inhibitor is hereinafter referred to as modified LHL (LHL-M).

Both reagents, LHL and LHL-M are used for the detection of PG, BC and LPS. This detection is based on the activation of the proPO system in lobster (FIG. 1). Therefore, the detection of PG, BC and LPS is performed by determining the enzyme activity of the active phenoloxidase (FO) or the peptidase activity of ppAs (FIG. 1).

The phenoloxidase activity is determined using monophenolic substrates (eg tyramine, L-tyrosine, 4-hydroxyphenylacetic acid, 4-hydroxyphenylpropionic acid) or diphenolic substrates (eg dihydroxy-L-phenylalanine (L-DOPA), dopamine, 3,4-dihydroxyphenylacetic acid, 3,4-dihydroxyphenylpropionic acid, catechol and methyl catechol. It is determined preferably with 1.2 mM dopamine. The formation of colored products allows the phenoloxidase activity can be determined visually or spectrophotometrically.

The sensitivity of the method to determine the phenoloxidase activity can be increased by the combination of monophenolic or o-diphenolic substrates with 3-methyl-2-benzothiazoline hydrazine (MBTH) or Besthorn's hydrazone. The MBTH is a powerful nucleophilic agent that forms a stable coloured adduct with o-quinones generated by phenoloxidases (MBTH-quinone), with an extinction coefficient or molar absorptivity much larger than the corresponding aminechrome [Espin J C et al., Eur J Biochem, 267:1270-1279, 2000; Garcia-Molina F et al., J. Agric. Food Chem 55:9739-9749, 2007]. The MBTH is used at a final concentration between 0.3 to 15 mM, preferably 2 to 7 mM.

The peptidase activity of ppA induced by BG, LPS and PG is determined using chromogenic or fluorogenic substrates for trypsin-like serine proteases. These substrates are of general formula R-Y or R-Arg-Lys-Y, where Y is a chromophore like p-nitroaniline (p-NA) or a fluorophore such as 7-amido-4-methyl coumarin, rhodamine, or 7-amido-4-trifluoro-methylcoumarin. R represents an L or D amino acid protected by its N-terminus by a protecting group, or a peptide comprising L or D amino acids, or their combination, protected at its N-terminus by a protecting group.

Assays for detection of PG, LPS and BG using the LHL or LHL-M reagent can be performed by kinetic, pseudo-kinetic or endpoint methods. The reaction can be detected by using conventional spectrophotometers and fluorimeters. However, due to higher sample throughput and saving of reagents, is preferred the using of microplate reader capable of reading 96 well microplates, equipped to read wavelengths in the visible, fluorescence, or those capable of performing both functions.

Kinetic assays are defined as the product detection in time immediately after the addition of all components of the reaction mixture including the substrate. Pseudo-kinetic assays are defined as those where the response is determined after substrate addition to a previously incubated reaction mixture. The endpoint assays are defined as the single reading of the response after a fixed time incubation of the reaction mixture with the substrate. The reaction mixture should have a pH value between 6 and 9, preferably 7.5, and may or may not contain divalent cations. It should contain calcium, magnesium or manganese in a minimum concentration of 5 mM, preferably 50 mM. The test temperature should be between room temperature and 45° C., preferably 37° C.

The present invention also comprises the use of LGBP to increase the sensitivity of both LHL and LHL-M to BG and LPS. The LGBP may be included in the formulation of the reagent, or can be added later to the reaction mixture. The LGBP may be in a concentration range in the assay for the detection of LPS and BG between 3 to 200 µg/ml, preferably from 50 to 125 µg/ml.

The LGBP is obtained from plasma, which is also a plentiful byproduct from the preparation of LHL. After an isoelectric precipitation step [Vargas-Albores F et al., Comp Biochem Physiol B Biochem Mol Biol, 116(4):453-458, 1997], the LGBP can be purified by affinity chromatography using hydrophilic matrices bound to (1,3)-β-D-glucans [Vargas-Albores F et al., Comp Biochem Physiol B Biochem Mol Biol, 116 (4): 453-458, 1997], immunoaffinity [Duvic B and Söderhäll K, J Biol. Chem., 265(16): 9327-9332, 1990] or heparin [Jimenez-Vegas F et at, Fish Shellfish Immunol 13(3):171-181, 2002]. Preferably, heparin is used as ligand, allowing the obtaining of large amounts of pure LGBP in a single chromatographic step.

EXAMPLES

Example 1

Preparation of Lobster Hemocyte Lysate (LHL)

Figure 1:
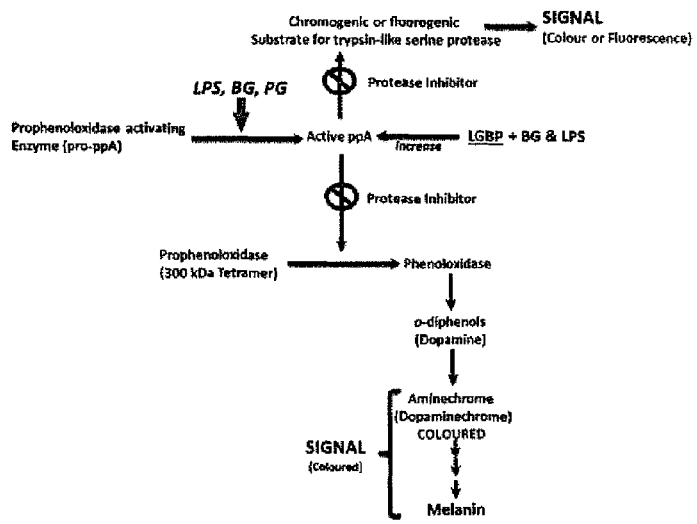
FIG. 1. Schematic representation of the prophenoloxidase activating system (proPO system) in the spiny lobster, and principle for the detection of lipopolysaccharides (LPS), peptidoglycans (PG) and (1,3)-β-D-glucans (BG) using the Lobster Hemocyte Lysate (LHL). LGBP: Lipopolysaccharide and (1,3)-β-D-glucans binding protein.
Figure 2:
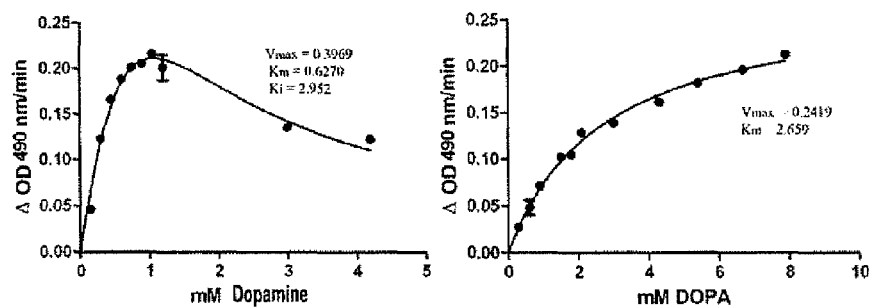
FIG. 2. Influence of concentrations of o-diphenolic substrates dopamine and L-DOPA on phenolixadase activity in the Lobster Hemocyte Lysate.
Figure 3:
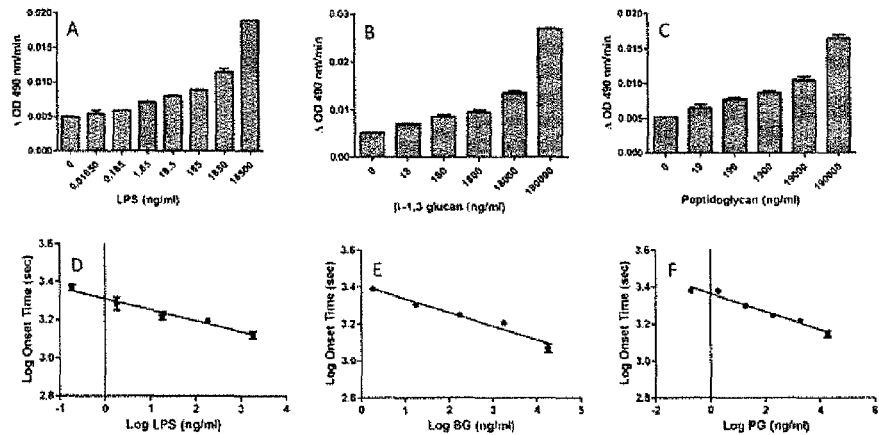
FIG. 3. LHL response to lipopolysaccharides (LPS), (1,3)-β-D-glucans (BG) and peptidoglycans (PG). Panels A-C: phenoloxidase activity in arbitrary units (Δ OD 490 nm/min). Panels D-F presents lineal relation between phenoloxidase activity and microbial elicitor concentration. LPS (0.185-1850 ng/ml), BG (1.8-18000 ng/ml) and PG (0.19-19000 ng/ml). Onset time means the reaction time required to reach a specific optical density at 490 nm.
Figure 4:
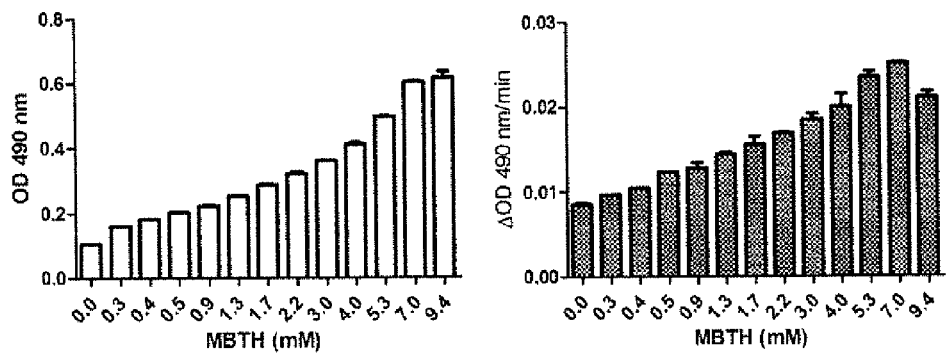
FIG. 4. Influence of the MBTH in the sensitivity of phenoloxidase response. Left panel: Optical density at 490 nm after 1 h at 37° C. (endpoint assay). Right panel: Reaction rate in absence (Control) and presence of different concentrations of MBTH.
Figure 5:
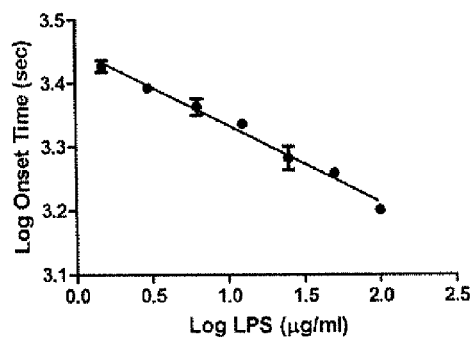
FIG. 5. Determination of proPO system response to LPS using chromogenic substrate for serine peptidase S-2222 (Bz-Ile-Glu(γ-OR)-Gly-Arg-pNA-HCl).
Figure 6:
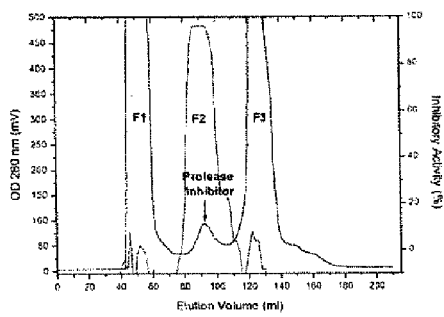
FIG. 6. Separation of protease inhibitor from the active components of proPO system by gel filtration chromatography in a Sephadex G-50 column.
Figure 7:
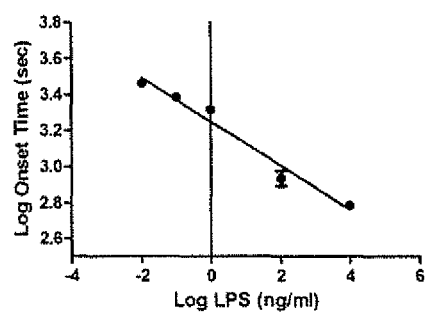
FIG. 7. Phenoloxidase response of LHL lacking protease inhibitor using dopamine as substrate. Sensitivity of 0.01 ng/ml LPS.
Figure 8:
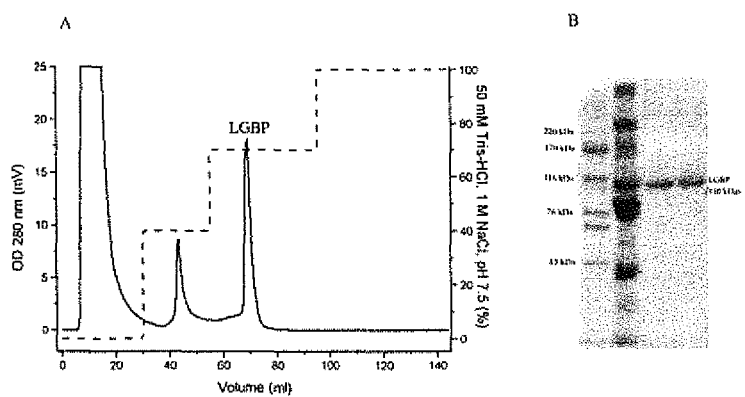
FIG. 8. Purification of LGBP by affinity chromatography in heparin-Sepharose CL-6B (Panel A). SDS-PAGE Electrophoresis (Panel B): Molecular weight marker (lane 1), whole plasma (lane 2), purified LGBP under reducing (lane 3) and non-reducing (lane 4) conditions. Proteins were stained with Coomassie Brilliant Blue R-250.

Ten milliliters of hemolymph were obtained from the fourth walking leg coxa using 20 ml sterile and pyrogen-free disposable syringes containing 10 ml of cold anticoagulant solution. The anticoagulant used was Alsever modified solution composed by 27 mM sodium citrate, 336 mM sodium chloride, 115 mM glucose, 9 mM EDTA, pH 7 (1000 mOsmol). The mixture of hemolymph:anticoagulant was poured into 50 ml sterile and pyrogen-free polypropylene centrifuge tubes and centrifuged at 700 g and 4° C. for 10 min. The supernatant containing plasma was discarded. Thereafter the pelleted hemocytes were washed to remove residual plasma components. To accomplish this, the hemocyte pellet was suspended with 20 ml of cold anticoagulant, and then the volume was raised up with anticoagulant to the original anticoagulant:hemolymph volume (50 ml), and centrifuged again as described above. The washing step was repeated once more. The washed hemocytes pellet was resuspended in 3 ml of lysis buffer composed by 50 mM Tris-HCl, 450 mM NaCl, pH 7.5, and then transferred to 13 mm×10 cm borosilicate tubes. The hemocyte suspension was lysed by sonication using three cycles of 20 Watts for 10 seconds in ice bath. The hemocyte homogenate was centrifuged at 13 000 rpm for 30 min. at 4° C. to obtain the clarified LHL.

Example 2

Comparing the Effect of Dopamine and L-DOPA Concentrations in the Sensitivity of Phenoloxidase Response in the LHL The lysate (420 µl at 0.1 mg/ml) was incubated with 4.2 ml of 1 mg/ml bovine trypsin for 30 min at 37° C. Hundred microliters of this mixture were added to the wells of a microplate containing 150 µl of various concentrations of L-DOPA (0.3 to 8 mM) or dopamine (0.15 to 9 mM) in 50 mM Tris-HCl, pH 7.5. The phenoloxidase activity was determined kinetically at 490 nm for 20 min at 37° C. in a microplate reader.

Example 3

Determination of PG, BG and LPS Using the LHL Through Detecting the Phenoloxidase Activity by Kinetic Method The LHL (12 mg/mg was diluted to 0.5 mg/ml with 50 mM Tris-HCl, pH 7.5. The assay was performed in 96-well flat-bottom microplates that were sterile and pyrogen free certified. The reaction mixture consisted of 150 µl of 50 mM Tris-HCl, pH 7.5, 50 mM $CaC_2$, 20 µl of LHL, and 50 µl of activator (LPS, PG or BG). Control was endotoxin free water. Finally, 50 µl of 3.75 mM dopamine was added as substrate. Dopaminechrome formation was assessed kinetically at 490 nm during 1 h by reading every 15 sec at 37° C. in a microplate reader. The reaction velocity (ΔOD 490/min) was determined from the linear portion of the plot between OD 490 nm vs. time. Alternatively, the onset time was determined as the time required for the reaction mixture to reach an absorbance value of 0.1. The plots of the logarithm of the onset time vs. the logarithm of PAMP concentration were lineal and useful for quantitative purposes.

Example 4

Effect of MBTH in Increasing the Phenoloxidase Response in the LHL Titration

The LHL at 0.8 mg/mL was diluted to 0.1 mg/mL with 50 mM Tris-HCl, pH 7.5. The assay was performed in flat-bottom-well microplates. The reaction mixture consisted of 40 µl of 50 mM Tris-HCl, pH 7.5, 160 µl 1 mg/ml trypsin dissolved in 50 mM Tris-HCl, pH 7.5, 10 µl of LHL and 40 µl of MBTH dissolved in distilled water. This mixture was incubated for 20 minutes at 37° C. and finally 50 µl of 3.75 mM dopamine were added to each well. The reaction was kinetically read at 490 nm for 1 h every 15 sec at 37° C. in a microplate reader.

Example 5

Determination of LHL Response Against LPS Using Chromogenic Substrates for Serine Peptidases Fifty microliters of LHL (1 mg/ml) obtained as described in Example 1, but without sodium chloride in the lysis buffer, were combined with 150 µl of 50 mM Tris-HCl, pH 7.5 buffers, and 50 µl of LPS. Thereafter, 50 µl of 0.6 mM chromogenic substrate S-2222 (Bz-Ile-Glu (γ-OR)-Gly-Arg-pNA-HCl) were added to each well. The p-nitroaniline released was kinetically detected at 405 nm for 1 h at 37° C.

Example 6

Protease Inhibitor Separation by Gel Filtration Chromatography

The protease inhibitor is separated from the active components of the proPO activating system in the LHL by using gel filtration chromatography on Sephadex G-50 superfine packed in a column XK 16/70 (Vt=131.4 ml) that was previously equilibrated with 50 mM Tris-HCl, 0.2 M NaCl, pH 7.5. Four milliliters of 8 mg/ml LHL (3% Vt) were fractionated at a flow rate of 0.3 ml/min. The chromatographic fractionations were monitored at 280 nm. The fraction corresponding to the void volume of the column was collected and designated as F1 or modified LHL (LHL-M).

Example 7

Protease Inhibitor Separation by Spin Column

The LHL was fractionated on a spin column packed with Sephadex G-50 (1.5 ml). The column was equilibrated with 50 mM Tris-HCl, 450 mM NaCl, pH 7.5 buffers by washing the column 4 times at 1000 rpm for 1 min. One hundred and fifty microliters of LHL, prepared as in Example 1, were applied to the spin column and centrifuged at 1000 rpm for 1 min. The eluate was collected, and both the LHL (also named FO fraction) and the eluate or fractionated LHL (also named F1 or LHL-M) were analyzed for protein concentration, inhibitory activity against trypsin, and phenoloxidase activity.

| Protein Concentration | | |
|---|---|---|
| F0 | 150 µl | 9.7 mg/ml |
| F1 | 150 µl | 3 mg/ml |
| Inhibitory Activity (IA) | | |
| | IA/ml | IA/mg |
| F0 | 2378.81 ± 258.938 | 225.55 ± 36.586 |
| F1 | 19.66 ± 0.277 | 6.598 ± 0.093 |
| Phenoloxidase Activity (PO) | | |
| | PO/ml | PO/mg |
| F0 | 0.265 ± 0.0240 | 1.366 ± 0.01240 |
| F1 | 0.089 ± 0.0090 | 1.483 ± 0.01650 |

Example 8

Determination of Phenoloxidase Response Against LPS in LHL Lacking Trypsin-Inhibitory Activity or LHL-M The lysate without inhibitor (Modified LHL; LHL-M) was obtained according to Example 5. The reaction mixture with 50 of LPS, 150 µl of Tris-HCl, 50 mM $CaCl_2$, pH 7.5, and 20 µl of 0.8 mg/ml lysate (LHL-M) were incubated at 37° C. for 30 min. Finally, 50 µl of 3.75 mM dopamine was added and the reaction progress was kinetically read at 490 nm for 1 hour at 37° C. The onset time was calculated as the time required to reach an optical density of 0.3, then the log of onset time vs. log of LPS concentrations was plotted.

Example 9

Purification of Lipopolysaccharide and β-1,3 Glucan Binding Protein (LGBP) from Plasma The plasma obtained during the LHL preparation was centrifuged for clarification at 5000 rpm for 20 min at 4° C. Hundred milliliters of clarified plasma were dialyzed vs. 5 L of distilled water at 4° C. for 48 hours using a dialysis membrane with a cutoff of 8000 Da. Four changes of dialyzing water every 12 hours were made during the period. The dialysate was centrifuged at 5000 rpm for 20 min at 4° C. and the supernatant was discarded. The protein pellet was suspended in 50 mM Tris-HCl, 0.2 M NaCl, pH 7.5 (Buffer A), and centrifuged again to remove the insoluble denatured proteins. Thirty-five milligrams of sample in 5 ml were applied to a column packed with Heparin-Sepharose CL-6B previously equilibrated in buffer A. After the elution of unbound proteins, the column was washed with 2.5 column volumes of a mixture of Buffer A:Buffer B (60:40 v/v). Buffer B was composed by 50 mM Tris-HCl, 1 M NaCl, pH 7.5. Finally, LGBP was eluted with 5 column volumes with Buffer A:Buffer B (30:70 v/v). The chromatographic process was performed at a flow rate of 1 ml/min and the protein fractions were detected at 280 nm.

The invention claimed is:

1. A process for detecting one or more pathogen associated molecular patterns (PAMPs) selected from the group consisting of lipopolysaccharides, peptidoglycans and 1,3-β-D-glucans in a sample, said process comprising the steps of:
   providing a lysate of lobster hemocytes containing the prophenoloxidase activating (ProPO) system; wherein said ProPO system in said lysate can be is activated by each one of said PAMPs upon contact;
   modifying said lysate by removing or inactivating peptidase inhibitors present in said lysate, to thereby provide a modified lysate of lobster hemocytes containing the ProPO system;
   contacting a sample with said modified lysate of lobster hemocytes containing the ProPO system, to form a reaction mixture; and
   detecting one or more of said PAMPs in said sample by measuring in said reaction mixture the peptidase activity of the prophenoloxidase activating enzyme or the activity of the phenoloxidase enzyme of said ProPO system;
   wherein said lysate of lobster hemocytes is obtained from a lobster in the infraorders Astacidea, Palinura (Achelata) or Thalassinidea; and wherein said step of modifying said lysate comprises the removal or inactivation of a trypsin-like peptidase inhibitor having a molecular weight of about 5 kDa.

2. The process according to claim 1, wherein the peptidase activity of the prophenoloxidase activating enzyme is determined with a chromogenic or fluorogenic substrate for trypsin-like serine proteases.

3. The process according to claim 1, wherein the peptidase activity is measured spectrophotometrically by kinetic, pseudo-kinetic or endpoint methods.

4. The process according to claim 1, wherein said step of contacting further comprises the step of:
adding to the reaction mixture an amount of between 3 and 200 μg/ml of lipopolysaccharide and 1,3-β-D-glucan binding protein (LGBP), isolated from the plasma of a lobster, so as to substantially increase the sensitivity of detection of lipopolysaccharides and 1,3-β-D-glucans.

5. The process according to claim 1, wherein said step of measuring in said reaction mixture the peptidase activity of the prophenoloxidase activating enzyme or the activity of the phenoloxidase enzyme of said ProPO system comprises kinetic, pseudo-kinetic or endpoint methods.

6. The process according to claim 1, wherein the activity of the phenoloxidase enzyme is measured using monophenolic or o-diphenolic substrates.

7. The process according to claim 6, wherein the monophenolic or o-diphenolic substrates further comprises 3-methyl-2-benzothiazolinone hydrazone (MBTH) in concentrations between 0.3 and 10 mM in the reaction mixture to increase the sensitivity of the phenoloxidase response.

8. The process according to claim 1, wherein said step of modifying said lysate comprises the removal of said peptidase inhibitor based on separation by molecular size and shape, affinity, immunoaffinity, or molecular charge.

9. The process according to claim 1, wherein said lysate of lobster hemocytes is a lysate of spiny lobster hemocytes.

10. The process according to claim 1, wherein said lysate of lobster hemocytes is a lysate of *Panulirus argus* hemocytes.

* * * * *

UNITED STATES PATENT AND TRADEMARK OFFICE
CERTIFICATE OF CORRECTION

PATENT NO. : 10,023,899 B2
APPLICATION NO. : 14/368697
DATED : July 17, 2018
INVENTOR(S) : Rolando Perdomo Morales et al.

Page 1 of 1

It is certified that error appears in the above-identified patent and that said Letters Patent is hereby corrected as shown below:

On the Title Page

Item [73], insert:
-- Centro de Investigacion Y Desarrollo de Medicamentos (CIDEM) --

Signed and Sealed this
Sixteenth Day of October, 2018

Andrei Iancu
*Director of the United States Patent and Trademark Office*